United States Patent
Church et al.

(10) Patent No.: US 11,685,942 B2
(45) Date of Patent: Jun. 27, 2023

(54) METHODS FOR MAKING POLYPEPTIDES INCLUDING D-AMINO ACIDS

(71) Applicant: President and Fellows of Harvard College, Cambridge, MA (US)

(72) Inventors: George M. Church, Brookline, MA (US); Po-Yi Huang, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 14 days.

(21) Appl. No.: 16/081,989

(22) PCT Filed: Mar. 3, 2017

(86) PCT No.: PCT/US2017/020569
§ 371 (c)(1),
(2) Date: Sep. 4, 2018

(87) PCT Pub. No.: WO2017/151997
PCT Pub. Date: Sep. 8, 2017

(65) Prior Publication Data
US 2020/0283817 A1 Sep. 10, 2020

Related U.S. Application Data

(60) Provisional application No. 62/303,425, filed on Mar. 4, 2016.

(51) Int. Cl.
*C12P 21/00* (2006.01)

(52) U.S. Cl.
CPC .................................. *C12P 21/00* (2013.01)

(58) Field of Classification Search
CPC ........... C12P 21/00; C12P 13/04; C12P 19/34; C12P 21/02; C12N 9/96; C12N 9/104; C12N 9/1025; C12N 15/11; C12N 15/67; C12N 15/09; C12N 15/111; C12N 2310/12; C07K 14/00; C07K 1/02; A61K 38/02
See application file for complete search history.

(56) References Cited

U.S. PATENT DOCUMENTS

2012/0164697 A1 6/2012 Brazeau et al.

FOREIGN PATENT DOCUMENTS

WO 00/45177 A1 8/2000
WO 2016/154675 A1 10/2016

OTHER PUBLICATIONS

Huang, P. (2014). Study on bacterial protein synthesis system toward the incorporation of D-amino acid & synthesis of 2'-deoxy-3'-mercapto-tRNA (Order No. 3626714). Available from ProQuest Dissertations and Theses Professional. (1558123748). (Year: 2014).*
Achenbach, J., et al. Outwitting EF-Tu and the ribosome: translation with D-amino acids. Nucleic Acids Research. May 30, 2015, vol. 43, No. 12; pp. 5687-5698. (Year: 2015).*
Doerfel, L.K. et al. EF-P Is Essential for Rapid Synthesis of Proteins Containing Consecutive Proline Residues. Science. Jan. 4, 2013. vol. 339, Issue 6115, pp. 85-88 and Supplementary Material, pp. 1-27. (Year: 2013).*
Dedkova, L.M., et al. Enhanced D-Amino Acid Incorporation into Protein by Modified Ribosomes. Journal of the American Chemical Society. May 10, 2003, vol. 125, No. 22; pp. 6616-6617. (Year: 2003).*
Achenbach, Jet al. Outwitting EF-Tu and the ribosome: translation with D-amino acids. Nucleic Acids Research. May 30, 2015, vol. 43, No. 12; pp. 5687-5698; abstract;; p. 5687,2nd col. 2nd paragraph; p. 5688, 1st col. 1st paragraph; p. 5688, 2nd col. 4th paragraph; p. 5688, 2nd col. 6th paragraph; p. 5689, 2nd col. 1st paragraph; p. 5690, 1st col. 1st paragraph; p. 5694,1st col. 1st paragraph; p. 5694, 1st col. 2nd paragraph; p. 5696, 1st col. 3rd paragraph; Figure 1; DOI: 10.1093/nar/gkv566.
Dedkova, LM et al. Enhanced D-Amino Acid Incorporation into Protein by Modified Ribosomes. Journal of the American Chemical Society. May 10, 2003, vol. 125, No. 22; pp. 6616-6617; p. 1, 1st col. 5th paragraph; p. 1, 2nd col. 1st paragraph; DOI: 10.1021/ja035141q.

* cited by examiner

*Primary Examiner* — Antonio Galisteo Gonzalez
*Assistant Examiner* — Khaleda B Hasan
(74) *Attorney, Agent, or Firm* — Banner & Witcoff, Ltd.

(57) ABSTRACT

A method of making a polypeptide including one or more D-amino acids is provided. The method includes combining a ribosome with protein translation factors including (1) a template encoding the polypeptide, wherein the template encoding the polypeptide includes one or more codons which have been recoded to accept a tRNA attached to a D-amino acid, (2) a plurality of L-amino acids and a plurality of corresponding tRNAs, (3) a plurality of D-amino acids and their corresponding aminoacyl tRNA synthetase or a plurality of tRNAs ligated with a D-amino acid, and (4) elongation factor P in a concentration of 2 to 20 micromolar, wherein translation of the template encoding the polypeptide occurs to produce the polypeptide including one or more D-amino acids.

18 Claims, 6 Drawing Sheets
Specification includes a Sequence Listing.

SEQUENCE LISTING

```
<160> NUMBER OF SEQ ID NOS: 3

<210> SEQ ID NO 1
<211> LENGTH: 314
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (75)..(77)
<223> OTHER INFORMATION: a, c, t, g, unknown or other

<400> SEQUENCE: 1
ggcgtaatac gactcactat agggttaact ttaacaagga gaaaacatg  gattacaagg       60 atgacgacga taagnnnctg tggatgaaga aaatgaaaaa ggactggaag  tatctcgatt      120
gggacatgga catgatggac tattggtgga tggatgacct gtggctggat  tacaaatggg     180
atgatcttat gctgatggat aagtacctgg atgatatgga tgatgattac  ttgatggata     240
tgatggacga ttgggatctc atgttatggt acctctacat gtatctcctg  gatgactggg     300
atatgtataa gtaa                                                         314
```

```
<210> SEQ ID NO 2
<211> LENGTH: 267
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (28)..(31)
<223> OTHER INFORMATION: a, c, u or g
<220> FEATURE:
<221> NAME/KEY: modified_base
<222> LOCATION: (33)..(34)
<223> OTHER INFORMATION: a, c, u or g
<220> FEATURE:
<221> NAME/KEY: modified_base
<222> LOCATION: (36)..(37)
<223> OTHER INFORMATION: a, c, u or g
<220> FEATURE:
<221> NAME/KEY: modified_base
<222> LOCATION: (39)..(40)
<223> OTHER INFORMATION: a, c, u or g
<220> FEATURE:
<221> NAME/KEY: modified_base
<222> LOCATION: (42)..(43)
<223> OTHER INFORMATION: a, c, u or g
<220> FEATURE:
<221> NAME/KEY: modified_base
<222> LOCATION: (45)..(46)
<223> OTHER INFORMATION: a, c, u or g
<220> FEATURE:
<221> NAME/KEY: modified_base
<222> LOCATION: (48)..(49)
<223> OTHER INFORMATION: a, c, u or g
<220> FEATURE:
<221> NAME/KEY: modified_base
<222> LOCATION: (51)..(52)
<223> OTHER INFORMATION: a, c, u or g
<220> FEATURE:
<221> NAME/KEY: modified_base
<222> LOCATION: (54)..(55)
<223> OTHER INFORMATION: a, c, u or g
<220> FEATURE:
<221> NAME/KEY: modified_base
<222> LOCATION: (57)..(58)
<223> OTHER INFORMATION: a, c, u or g
<220> FEATURE:
<221> NAME/KEY: modified_base
<222> LOCATION: (60)..(61)
<223> OTHER INFORMATION: a, c, u or g
<220> FEATURE:
<221> NAME/KEY: modified_base
<222> LOCATION: (63)..(64)
<223> OTHER INFORMATION: a, c, u or g
<220> FEATURE:
<221> NAME/KEY: modified_base
<222> LOCATION: (66)..(67)
<223> OTHER INFORMATION: a, c, u or g
<220> FEATURE:
<221> NAME/KEY: modified_base
<222> LOCATION: (69)..(70)
<223> OTHER INFORMATION: a, c, u or g
<220> FEATURE:
<221> NAME/KEY: modified_base
<222> LOCATION: (72)..(73)
<223> OTHER INFORMATION: a, c, u or g
<220> FEATURE:
<221> NAME/KEY: modified_base
<222> LOCATION: (75)..(76)
<223> OTHER INFORMATION: a, c, u or g
<220> FEATURE:
<221> NAME/KEY: modified_base
<222> LOCATION: (78)..(79)
<223> OTHER INFORMATION: a, c, u or g
<220> FEATURE:
<221> NAME/KEY: modified_base
```

```
<222> LOCATION: (81)..(82)
<223> OTHER INFORMATION: a, c, u or g
<220> FEATURE:
<221> NAME/KEY: modified_base
<222> LOCATION: (84)..(85)
<223> OTHER INFORMATION: a, c, u or g
<220> FEATURE:
<221> NAME/KEY: modified_base
<222> LOCATION: (87)..(88)
<223> OTHER INFORMATION: a, c, u or g
<220> FEATURE:
<221> NAME/KEY: modified_base
<222> LOCATION: (90)..(91)
<223> OTHER INFORMATION: a, c, u or g
<220> FEATURE:
<221> NAME/KEY: modified_base
<222> LOCATION: (93)..(94)
<223> OTHER INFORMATION: a, c, u or g
<220> FEATURE:
<221> NAME/KEY: modified_base
<222> LOCATION: (96)..(97)
<223> OTHER INFORMATION: a, c, u or g
<220> FEATURE:
<221> NAME/KEY: modified_base
<222> LOCATION: (99)..(100)
<223> OTHER INFORMATION: a, c, u or g
<220> FEATURE:
<221> NAME/KEY: modified_base
<222> LOCATION: (102)..(103)
<223> OTHER INFORMATION: a, c, u or g
<220> FEATURE:
<221> NAME/KEY: modified_base
<222> LOCATION: (105)..(106)
<223> OTHER INFORMATION: a, c, u or g
<220> FEATURE:
<221> NAME/KEY: modified_base
<222> LOCATION: (108)..(109)
<223> OTHER INFORMATION: a, c, u or g
<220> FEATURE:
<221> NAME/KEY: modified_base
<222> LOCATION: (111)..(112)
<223> OTHER INFORMATION: a, c, u or g
<220> FEATURE:
<221> NAME/KEY: modified_base
<222> LOCATION: (114)..(115)
<223> OTHER INFORMATION: a, c, u or g
<220> FEATURE:
<221> NAME/KEY: modified_base
<222> LOCATION: (117)..(118)
<223> OTHER INFORMATION: a, c, u or g
<220> FEATURE:
<221> NAME/KEY: modified_base
<222> LOCATION: (120)..(121)
<223> OTHER INFORMATION: a, c, u or g
<220> FEATURE:
<221> NAME/KEY: modified_base
<222> LOCATION: (123)..(124)
<223> OTHER INFORMATION: a, c, u or g
<220> FEATURE:
<221> NAME/KEY: modified_base
<222> LOCATION: (126)..(127)
<223> OTHER INFORMATION: a, c, u or g
<220> FEATURE:
<221> NAME/KEY: modified_base
<222> LOCATION: (129)..(130)
<223> OTHER INFORMATION: a, c, u or g
<220> FEATURE:
<221> NAME/KEY: modified_base
<222> LOCATION: (132)..(133)
<223> OTHER INFORMATION: a, c, u or g
<220> FEATURE:
<221> NAME/KEY: modified_base
<222> LOCATION: (135)..(136)
<223> OTHER INFORMATION: a, c, u or g
<220> FEATURE:
<221> NAME/KEY: modified_base
<222> LOCATION: (138)..(139)
<223> OTHER INFORMATION: a, c, u or g
<220> FEATURE:
```

-continued

```
<221> NAME/KEY: modified_base
<222> LOCATION: (141)..(142)
<223> OTHER INFORMATION: a, c, u or g
<220> FEATURE:
<221> NAME/KEY: modified_base
<222> LOCATION: (144)..(145)
<223> OTHER INFORMATION: a, c, u or g
<220> FEATURE:
<221> NAME/KEY: modified_base
<222> LOCATION: (147)..(148)
<223> OTHER INFORMATION: a, c, u or g
<220> FEATURE:
<221> NAME/KEY: modified_base
<222> LOCATION: (150)..(151)
<223> OTHER INFORMATION: a, c, u or g
<220> FEATURE:
<221> NAME/KEY: modified_base
<222> LOCATION: (153)..(154)
<223> OTHER INFORMATION: a, c, u or g
<220> FEATURE:
<221> NAME/KEY: modified_base
<222> LOCATION: (156)..(157)
<223> OTHER INFORMATION: a, c, u or g
<220> FEATURE:
<221> NAME/KEY: modified_base
<222> LOCATION: (159)..(160)
<223> OTHER INFORMATION: a, c, u or g
<220> FEATURE:
<221> NAME/KEY: modified_base
<222> LOCATION: (162)..(163)
<223> OTHER INFORMATION: a, c, u or g
<220> FEATURE:
<221> NAME/KEY: modified_base
<222> LOCATION: (165)..(166)
<223> OTHER INFORMATION: a, c, u or g
<220> FEATURE:
<221> NAME/KEY: modified_base
<222> LOCATION: (168)..(169)
<223> OTHER INFORMATION: a, c, u or g
<220> FEATURE:
<221> NAME/KEY: modified_base
<222> LOCATION: (171)..(172)
<223> OTHER INFORMATION: a, c, u or g
<220> FEATURE:
<221> NAME/KEY: modified_base
<222> LOCATION: (174)..(175)
<223> OTHER INFORMATION: a, c, u or g
<220> FEATURE:
<221> NAME/KEY: modified_base
<222> LOCATION: (177)..(178)
<223> OTHER INFORMATION: a, c, u or g
<220> FEATURE:
<221> NAME/KEY: modified_base
<222> LOCATION: (180)..(181)
<223> OTHER INFORMATION: a, c, u or g
<220> FEATURE:
<221> NAME/KEY: modified_base
<222> LOCATION: (183)..(184)
<223> OTHER INFORMATION: a, c, u or g
<220> FEATURE:
<221> NAME/KEY: modified_base
<222> LOCATION: (186)..(187)
<223> OTHER INFORMATION: a, c, u or g
<220> FEATURE:
<221> NAME/KEY: modified_base
<222> LOCATION: (189)..(190)
<223> OTHER INFORMATION: a, c, u or g
<220> FEATURE:
<221> NAME/KEY: modified_base
<222> LOCATION: (192)..(193)
<223> OTHER INFORMATION: a, c, u or g
<220> FEATURE:
<221> NAME/KEY: modified_base
<222> LOCATION: (195)..(196)
<223> OTHER INFORMATION: a, c, u or g
<220> FEATURE:
<221> NAME/KEY: modified_base
<222> LOCATION: (198)..(199)
<223> OTHER INFORMATION: a, c, u or g
```

-continued

```
<220> FEATURE:
<221> NAME/KEY: modified_base
<222> LOCATION: (201)..(202)
<223> OTHER INFORMATION: a, c, u or g
<220> FEATURE:
<221> NAME/KEY: modified_base
<222> LOCATION: (204)..(205)
<223> OTHER INFORMATION: a, c, u or g
<220> FEATURE:
<221> NAME/KEY: modified_base
<222> LOCATION: (207)..(208)
<223> OTHER INFORMATION: a, c, u or g
<220> FEATURE:
<221> NAME/KEY: modified_base
<222> LOCATION: (210)..(211)
<223> OTHER INFORMATION: a, c, u or g
<220> FEATURE:
<221> NAME/KEY: modified_base
<222> LOCATION: (213)..(214)
<223> OTHER INFORMATION: a, c, u or g
<220> FEATURE:
<221> NAME/KEY: modified_base
<222> LOCATION: (216)..(217)
<223> OTHER INFORMATION: a, c, u or g
<220> FEATURE:
<221> NAME/KEY: modified_base
<222> LOCATION: (219)..(220)
<223> OTHER INFORMATION: a, c, u or g
<220> FEATURE:
<221> NAME/KEY: modified_base
<222> LOCATION: (222)..(223)
<223> OTHER INFORMATION: a, c, u or g
<220> FEATURE:
<221> NAME/KEY: modified_base
<222> LOCATION: (225)..(226)
<223> OTHER INFORMATION: a, c, u or g
<220> FEATURE:
<221> NAME/KEY: modified_base
<222> LOCATION: (228)..(229)
<223> OTHER INFORMATION: a, c, u or g
<220> FEATURE:
<221> NAME/KEY: modified_base
<222> LOCATION: (231)..(232)
<223> OTHER INFORMATION: a, c, u or g
<220> FEATURE:
<221> NAME/KEY: modified_base
<222> LOCATION: (234)..(235)
<223> OTHER INFORMATION: a, c, u or g
<220> FEATURE:
<221> NAME/KEY: modified_base
<222> LOCATION: (237)..(238)
<223> OTHER INFORMATION: a, c, u or g
<220> FEATURE:
<221> NAME/KEY: modified_base
<222> LOCATION: (240)..(241)
<223> OTHER INFORMATION: a, c, u or g
<220> FEATURE:
<221> NAME/KEY: modified_base
<222> LOCATION: (243)..(244)
<223> OTHER INFORMATION: a, c, u or g
<220> FEATURE:
<221> NAME/KEY: modified_base
<222> LOCATION: (246)..(247)
<223> OTHER INFORMATION: a, c, u or g
<220> FEATURE:
<221> NAME/KEY: modified_base
<222> LOCATION: (249)..(250)
<223> OTHER INFORMATION: a, c, u or g
<220> FEATURE:
<221> NAME/KEY: modified_base
<222> LOCATION: (252)..(253)
<223> OTHER INFORMATION: a, c, u or g
<220> FEATURE:
<221> NAME/KEY: modified_base
<222> LOCATION: (255)..(256)
<223> OTHER INFORMATION: a, c, u or g
<220> FEATURE:
<221> NAME/KEY: modified_base
<222> LOCATION: (258)..(259)
```

```
<223> OTHER INFORMATION: a, c, u or g
<220> FEATURE:
<221> NAME/KEY: modified_base
<222> LOCATION: (261)..(262)
<223> OTHER INFORMATION: a, c, u or g
<220> FEATURE:
<221> NAME/KEY: modified_base
<222> LOCATION: (264)..(264)
<223> OTHER INFORMATION: a, c, u or g
<220> FEATURE:
<223> OTHER INFORMATION: See specification as filed for detailed
      description of substitutions and preferred embodiments

<400> SEQUENCE: 2
auggauuaca aggaugacga cgauaagnnn ndnndnndnn dnndnndnnd nndnndnndn      60
ndnndnndnn dnndnndnnd nndnndnndn ndnndnndnn dnndnndnnd nndnndnndn     120
ndnndnndnn dnndnndnnd nndnndnndn ndnndnndnn dnndnndnnd nndnndnndn     180
ndnndnndnn dnndnndnnd nndnndnndn ndnndnndnn dnndnndnnd nndnndnndn     240
ndnndnndnn dnndnndnnd nndnuaa                                         267

<210> SEQ ID NO 3
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(88)
<223> OTHER INFORMATION: Asp, Tyr, Lys, Met, Trp or Leu
<220> FEATURE:
<223> OTHER INFORMATION: See specification as filed for detailed
      description of substitutions and preferred embodiments

<400> SEQUENCE: 3

Met Asp Tyr Lys Asp Asp Asp Asp Lys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
                85
```

METHODS FOR MAKING POLYPEPTIDES INCLUDING D-AMINO ACIDS

RELATED APPLICATION DATA

This application is a National Stage Application under 35 U.S.C. 371 of co-pending PCT application PCT/US17/20569 designating the United States and filed Mar. 3, 2017; which claims the benefit of U.S. provisional application No. 62/303,425 and filed Mar. 4, 2016 each of which are hereby incorporated by reference in their entireties.

STATEMENT OF GOVERNMENT INTERESTS

This invention was made with government support under DE-FG02-02ER63445 awarded by Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on Sep. 4, 2018, is named "Sequence Listing.txt" and is 8192 bytes in size.

FIELD

The present invention relates in general to methods of making polypeptides including D-amino acids.

BACKGROUND

D-amino acid containing peptides (DAACP) are widely present in microbial, fungal and amphibian secretions. See, Ollivaux, C., Soyez, D. & Toullec, J.-Y. Biogenesis of d-amino acid containing peptides/proteins: where, when and how? *J. Pept. Sci.* 20, 595-612 (2014). In nature, these molecules are made through non-ribosomal pathways, such as non-ribosomal peptide synthesis or post-translational modification, i.e. epimerization. D-amino acid containing protein and peptides, mimicking the concept of DAACP, have been shown to have prolonged half-life in serum and resistance toward proteases without immunogenicity. See also, Achenbach et al., *Nucleic Acids Res.* 43, 5687-5698 (2015); Fujino, T., Goto, Y., Suga, H. & Murakami, H. Reevaluation of the d-Amino Acid Compatibility with the Elongation Event in Translation. *J. Am. Chem. Soc.* 135, 1830-1837 (2013); Dedkova, L. M., Fahmi, N. E., Golovine, S. Y. & Hecht, S. M. Enhanced d-Amino Acid Incorporation into Protein by Modified Ribosomes. *J. Am. Chem. Soc.* 125, 6616-6617 (2003); and Englander, M. T. et al. The ribosome can discriminate the chirality of amino acids within its peptidyl-transferase center. *Proc. Natl. Acad. Sci.* 112, 6038-6043 (2015). However, natural protein synthesis systems provide barriers to D-amino acid incorporation into polypeptides.

SUMMARY

The disclosure provides methods of making polypeptides including one or more D-amino acids where EF-P is included in the reaction volume with translation reagents and components. The disclosure provides a method of making a polypeptide including one or more D-amino acids including combining protein translation factors including a ribosome with (1) a template encoding the polypeptide, wherein the template encoding the polypeptide includes one or more codons which have been recoded to accept a tRNA attached to a D-amino acid, (2) a plurality of L-amino acids and a plurality of corresponding tRNAs, (3) a plurality of D-amino acids and their corresponding aminoacyl tRNA synthetase or a plurality of tRNAs ligated with a D-amino acid, and (4) elongation factor P in a concentration of about 1 to about 20 micromolar, wherein translation of the template encoding the polypeptide occurs to produce the polypeptide including one or more D-amino acids. The disclosure provides that the concentration of elongation factor P is about 2 to about 16 micromolar. The disclosure provides that the concentration of elongation factor P is about 4 to about 8 micromolar. The disclosure provides that the codons are amber stop codons. The disclosure provides that the template is a mRNA template encoding the polypeptide. The disclosure provides that the template is a DNA template encoding the polypeptide. The disclosure provides that the tRNA corresponding to the D-amino acids have a high binding affinity to elongation factor thermo unstable (EF-Tu). The disclosure provides that the tRNA corresponding to the D-amino acids are backbone-optimized to promote binding between the tRNA and elongation factor thermo unstable. The disclosure provides that the ribosome is a mutant ribosome having enhanced $^{D}$AA incorporation capability. The disclosure provides that the method is carried out in an in vitro protein synthesis solution.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which.

DETAILED DESCRIPTION

The present disclosure provides methods of making polypeptides including one or more D-amino acids using a mRNA template or DNA template encoding the polypeptide. The methods may be performed in vitro or in vivo, such as in a genomically recoded organism. The polypeptides may also include one or more L-amino acids. Amino acids within the scope of the present disclosure include Glycine, Alanine, Valine, Leucine, Isoleucine, Serine, Cysteine, Selenocysteine, Threonine, Methionine, Proline and its derivatives, Phenylalanine, Tyrosine, Tryptophan, Histidine, Lysine and its derivatives, Pyrrolysine, Arginine, Aspartate, Glutamate, Asparagine, and Glutamine. Amino acid activation, i.e. the attachment of an amino acid to its transfer RNA (tRNA) using its corresponding aminoacyl tRNA synthetase is well known in the art. Each amino acid is recognized by its specific aminoacyl-tRNA synthetase. The synthetases are usually composed of one to four protein subunits. The enzymes vary considerably in structure although they all perform the same type of reaction by binding ATP, one specific amino acid and its corresponding tRNA.

The mRNA template or DNA template encoding the polypeptide may include one or more codons, such as amber stop codons, which have been recoded to accept a tRNA attached to a D-amino acid. Codons can be reassigned to incorporate D-amino acids using methods known to those of skill in the art. See Lajoie, M. J. et al. Probing the limits of genetic recoding in essential genes. *Science* 342, 361-363, doi:10.1126/science.1241460 (2013) hereby incorporated by reference in its entirety. See also, Anderson, J. C. et al. An expanded genetic code with a functional quadruplet codon. *Proc. Natl. Acad. Sci. U.S.A* 101, 7566-7571, doi:10.1073/pnas.0401517101 (2004), Neumann, H., Wang, K., Davis, L., Garcia-Alai, M. & Chin, J. W. Encoding multiple unnatural amino acids via evolution of a quadruplet-decoding ribosome. *Nature* 464, 441-444, (2010) and Chatterjee, A., Lajoie, M. J., Xiao, H., Church, G. M. & Schultz, P. G. A Bacterial Strain with a Unique Quadruplet Codon Specifying Non-native Amino Acids. *Chembiochem*, n/a-n/a, doi: 10.1002/cbic.201402104 (2014) each of which are hereby incorporated by reference in its entirety.

Figure 1A:
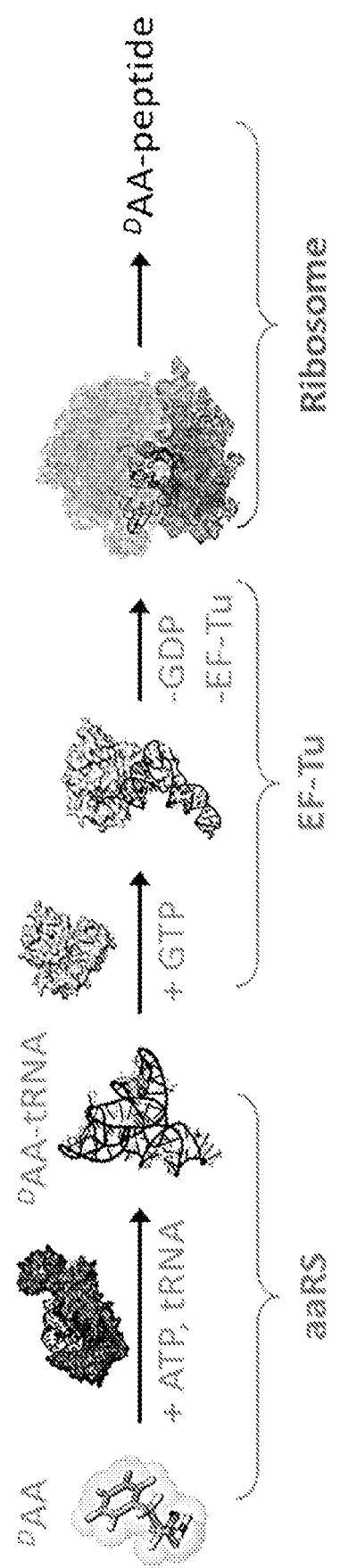
FIG. 1A depicts a method of making a polypeptide including one or more D-amino acids.

The present disclosure provides the use of RNA ligase to attach a D-amino acyl-dinucleotide to a corresponding tRNA. The present disclosure provides use of elongation factor thermo unstable ("EF-Tu") to promote interaction between the ribosome and the tRNA with a D-amino acid attached thereto. The EF-Tu may bind to the tRNA with the D-amino acid attached thereto and GTP to form a ternary complex. The tRNA may be backbone-optimized to increase binding between EF-Tu and the tRNA with the D-amino acid attached thereto. The present disclosure provides an assay for determining ribosomal activity, i.e. catalysis, to incorporate the D-amino acid into a growing peptide chain. Each of these aspects of the present disclosure is shown in FIG. 1A. General steps of RNA translation and D-amino acid barriers in protein translation are provided in Ahmad, S. et al. Mechanism of chiral proofreading during translation of the genetic code. *Elife* 2, e01519 (2013) hereby incorporated by reference in its entirety.

Cell-free translation or cell-free transcription and translation systems including templates, ribosomes and other reagents are known to those of skill in the art and are used for in vitro protein synthesis. One example is the PURExpress system commercially available from New England Biolabs, Inc. in vitro or cell-free translation systems include all the macromolecular components (70S or 80S ribosomes, tRNAs, aminoacyl-tRNA synthetases, initiation, elongation and termination factors, etc.) required for translation of exogenous RNA. Extracts may be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors (Mg2+, K+, etc.). in vitro translation systems may use RNA or DNA as the starting genetic material template. Systems that start with DNA templates transcribe the DNA template into RNA which is then translated. Exemplary cell-free translation systems include rabbit reticulocyte lysate, wheat germ extract, *E. coli* cell-free system and linked or coupled transcription/translation systems.

The following examples are set forth as being representative of the present disclosure. These examples are not to be construed as limiting the scope of the present disclosure as these and other equivalent embodiments will be apparent in view of the present disclosure, figures and accompanying claims.

Example I

Materials and Methods

Preparation of L-Amino Acyl-tRNAs and D-Amino Acyl-tRNAs

Synthesis of pdCpA was carried out using the methods of Ellman, J., Mendel, D., Anthony-Cahill, S., Noren, C. J. & Schultz, P. G. [15] Biosynthetic method for introducing unnatural amino acids site-specifically into proteins. *Methods Enzymol.* 202, 301-336 (1991) hereby incorporated by reference in its entirety. NPPOC protected amino acids are described in Bhushan, K. R., DeLisi, C., & Laursen, R. A. (2003). Synthesis of photolabile 2-(2-nitrophenyl)propyloxycarbonyl protected amino acids. *Tetrahedron Letters,* 44(47), 8585-8588. Identity and purity of all substrates are confirmed by either HRES-MS, NMR or both. In vitro transcriptions of tRNAs were carried out as follows: prepare 300 μL mixture of 4 mM NTPs, 0.5 U/μL Murine RNase Inhibitor (New England Biolab Inc.), 10 mM DTT, 100 μg/mL T7 RNA polymerase, 125 μg/mL inorganic pyrophosphatase, 1×T7 transcription buffer (contains 40 mM Tris-HCl pH 8.1, 20 mM MgCl$_2$, 0.1% Triton X-100, 30 mM Spermidine and 500 μg/mL BSA) and optional 10% DMSO (for tRNA$^{Glu2}$ synthesis) and incubate with template DNA oligonucleotides (Integrated DNA technologies) at 42° C. for 2.5 hr. After that, 200 μL mixture of same components except with 10 mM NTPs, 30 mM MgCl$_2$ and 20 μg/mL T7 RNA polymerase is added into previous reaction, and further incubate at 38° C. overnight. The product is washed with acid phenol twice and with 24:1 chloroform-isoamyl alcohol twice, and then precipitated with 500 μL of isopropanol. Crude RNAs are purified by 15% denaturing PAGE gel.

Ligation of aa-pdCpA to tRNA$_{C-3'}$ is carried out as follows: For a 200 μL reaction, mix the components on ice in the following order: 8 μL of 5 mM aa-pdCpA, 20 μL DMSO, 102 μL of water, 20 μL of 10×T4 ligation buffer (contains 500 mM Hepes-KOH pH 7.5, 150 mM MgCl$_2$ and 7.5 mM ATP), 20 μL of 400 μM tRNA$_{C-3'}$ and 30 μL of 10 kU/mL T4 RNA Ligase (New England Biolab Inc.). After incubation at 37° C. for 45 min, 30 μL of 2M NaOAc pH 4.5 is added to quench reaction and N-protected aa-tRNA is recovered by EtOH precipitation and quantified by Qubit 2.0 Fluorometer. Right before use, chemically acylated aa-tRNAs are illuminated with 100W, 350 nm UV (B100-AP from UVP LLC.) for 10 min on ice to remove NPPOC protecting group.

Protein Purification and Construction of PURE Translation Reaction

Overexpression and purification of aaRSes and translation factors is carried out based on the methods of Shimizu, Y. et al. Cell-free translation reconstituted with purified components. *Nat. Biotechnol.* 19, 751-5 (2001) hereby incorporated by reference in its entirety, with slight modifications. Ribosome is purified from strain RB1 (see Wang, H. H., Huang, P.-Y., Xu, G., Haas, W., Marblestone, A., Li, J., Church, G. M. (2012). Multiplexed in vivo His-tagging of enzyme pathways for in vitro single-pot multienzyme catalysis. ACS Synthetic Biology, 1(2), 43-52 hereby incorporated by reference in its entirety) following same procedure as Shimizu et al. PURE translation master mix cocktail with limited aaRS and amino acids are prepared as follow. Solution A (5×) contains: 10 mM ATP, 10 mM GTP, 5 mM CTP, 5 mM UTP, 100 mM phosphocreatine, 250 mM Hepes-KOH pH 7.60, 500 mM KOAc, 65 mM Mg(OAc)$_2$, 10 mM Spermidine, 5 mM DTT, 50 µg/mL formyl donor$^3$. Solution B (10×) without EF-Tu contains: 12.12 µM IF1, 4.11 µM IF2, 4.86 µM IF3, 16.43 µM EF-Ts, 6.44 µM EF-G, 1.21 µM AspRS, 0.86 µM GlyRS, 1.09 µM LysRS, 0.28 µM MetRS, 0.29 µM TrpRS, 0.13 µM TyrRS, 5.85 µM fmt, 0.89 µM rabbit muscle creatine kinase, 1.15 µM yeast myokinase, 0.64 µM nucleotide diphosphate kinase, 1.01 µM T7 RNA polymerase, 0.46 µM inorganic pyrophosphatase. Translation reaction is mixed as follow: prepare solutions on ice containing 1×Solution A, 1.36 mg/mL deacylated total tRNA (MRE600 total tRNA from Roche, incubate in pH 8.0, 250 mM NaBO$_4$ buffer for 1 hr at 37° C. and then cleaned up by Zeba-desalting column), 0.1 mM of each amino acid (Met, Asp, Gly, Tyr, Trp, Leu and Lys), 1×Solution B, 1.2 µM ribosome, 25 µM EF-Tu, 4 ng/µL DNA template. Incubate mixture at 37° C. for 1 hr right after addition of 24 µM photo-deprotected aa-tRNA. The actual EF-Tu and aa-tRNA concentrations used are described in each figure, otherwise 25 µM of EF-Tu and 24 µM of aa-tRNA are used.

Plasmid pST39/His-EFP/YjeA/YjeK, which encoding EF-P and its modification enzymes is obtained from Dr. Park Myung Hee at NIH. Overexpression and purification procedure of EF-P protein is adapted from Park, J.-H., Johansson, H. E., Aoki, H., Huang, B. X., Kim, H.-Y., Ganoza, M. C., & Park, M. H. (2012). Post-translational Modification by β-Lysylation Is Required for Activity of *Escherichia coli* Elongation Factor P (EF-P). Journal of Biological Chemistry, 287(4), 2579-2590.

Western Blot Analysis of Expressed Peptides

DNA Templates for the read-through assay are custom synthesized (Integrated DNA Technology) with sequence below (bold: translation initiation site; lower case: FLAG tag; underscore: unassigned codon, such as TAG or consecutive TAG-TAG):

5'GGCGTAATACGACTCACTATAGGGTTAACTTTAACAAGGAGAAAAACA

TGgattacaaggatgacgacgataag<u>NNN</u>CTGTGGATGAAGAAAATGAAA

AAGGACTGGAAGTATCTCGATTGGGACATGGACATGATGGACTATTGGTG

GATGGATGACCTGTGGCTGGATTACAAATGGGATGATCTTATGCTGATGG

ATAAGTACCTGGATGATATGGATGATGATTACTTGATGGATATGATGGAC

GATTGGGATCTCATGTTTATGGTACCTCTACATGTATCTCCTGGATGACTG

GGATATGTATAAGTAA3'.

Translation reactions are quenched with equal volume of 2×tricine SDS sample buffer (Life Technology) and analyzed on 16% Tricine protein gel. Proteins are transferred to PVDF membranes by iBlot® (Life technology, setting program=P3, duration=3 min 40 sec), and then blotted by anti-FLAG M2 antibody (Sigma F1804) and detected by SuperSignal West Femto kit (Pierce) and imaged by Bio-rad ChemiDoc™ MP system.

Example II

Assessing Amino Acid Incorporation Using Translational Machinery

Experiments are carried out to determine the ability of the translational machinery to discriminate between L-amino acids and D-amino acids without interference from D-amino acid oxidase and D-aminoacyl-tRNA deacylase using the PURE system, which is a purified *E. coli*, protein synthesis machinery. See Shimizu, Y. et al. Cell-free translation reconstituted with purified components. *Nat. Biotechnol.* 19, 751-5 (2001) hereby incorporated by reference in its entirety. Chemically acylated D-aminoacyl-tRNA is used as model system to engineer a D-amino acid tolerating translation machinery. See Ellman, J., Mendel, D., Anthony-Cahill, S., Noren, C. J. & Schultz, P. G. [15] Biosynthetic method for introducing unnatural amino acids site-specifically into proteins. *Methods Enzymol.* 202,301-336 (1991) hereby incorporated by reference in its entirety.

Figure 1B:
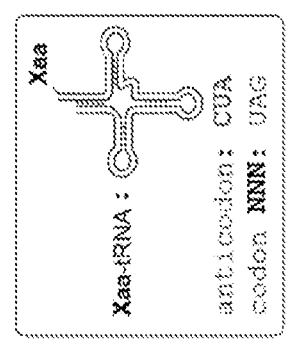
FIG. 1B depicts aspects of the protein translation read through assay described herein including a mRNA template encoding N-terminus FLAG epitope and a C-terminus stretch of artificial peptide composed of six different amino acids, either with or without an amber codon in between. (SEQ ID NOs: 2 and 3)

An amber codon read through assay is adapted from Fujino, T., Goto, Y., Suga, H. & Murakami, H. Reevaluation of the d-Amino Acid Compatibility with the Elongation Event in Translation. *J. Am. Chem. Soc.* 135, 1830-1837 (2013) hereby incorporated by reference in its entirety with slight modification to assess D-amino acid incorporation during elongation. In brief, mRNA templates encoding N-terminus FLAG epitope and a C-terminus stretch of artificial peptide composed of six different amino acids, either with or without an amber codon in between as depicted in FIG. 1B, are subjected to in vitro translation with purified ribosome, translational factors and aminoacyl-tRNA synthetases, in the presence or absence of amber codon suppressor tRNA chemically acylated with D-amino acid or L-amino acid. The produced peptides are resolved in denaturing PAGE gel and visualized by western blotting with anti-FLAG antibody.

Figure 1C:
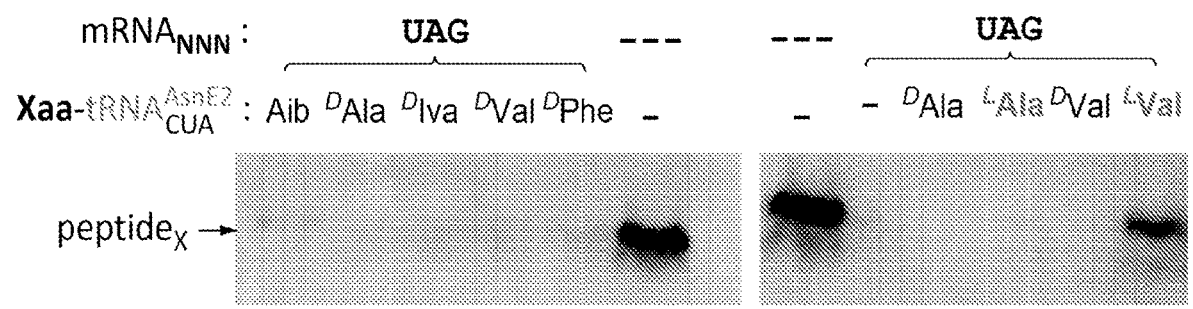
FIG. 1C depicts a Western blot of $^{L/D}$AA (amino acid) read-through assay carried by AsnE2-tRNA body.

When examining the incorporation of various L-amino acid, D-amino acid, and α, α-dialkylamino acids with the orthogonal suppressor AsnE2 tRNA$_{CUA}$ antibody (see Goto, Y., Katoh, T. & Suga, H. Flexizymes for genetic code reprogramming. *Nat. Protoc.* 6, 779-90 (2011) hereby incorporated by reference in its entirety), L-valine yielded measurable incorporation, while L-alanine and others did not, indicating a barrier to incorporation. See FIG. 1C. mRNA with label " - - - " is a template without middle NNN codon which does not require chemically acylated tRNA.

Example III

Identifying tRNA Having Strong Affinity to EF-Tu-GTP

Experiments are carried out to identify tRNA having a strong affinity to EF-Tu-GTP and therefore, a sufficient affinity to D-aminoacyl-tRNA to promote incorporation into a growing polypeptide chain using translational machinery.

The specificity of EF-Tu-GTP for the tRNA body sequence is thermodynamically compensated by the cognate aminoacyl ester. See Dale, T., Sanderson, L. E. & Uhlenbeck, 0. C. The Affinity of Elongation Factor Tu for an Aminoacyl-tRNA Is Modulated by the Esterified Amino Acid†. *Biochemistry* 43, 6159-6166 (2004). Estimated association constants ($K_D$) of EF-Tu with $^L$Val-tRNA$^{AsnE2}$ and $^L$Ala-tRNA$^{AsnE2}$ are 16 nM and 96 nM respectively, while the average $K_D$ of 20 $^L$AA-tRNA bodies falling between 10 to 40 nM. See Table 1 below.

| Year, Lab | Translation system | [EF-Tu], μM | [aa-tRNA$^{aaRS}$], μM | [aa$^{mis}$-tRNA], μM |
|---|---|---|---|---|
| — | *E. coli* cell (mid-log phase) | ca. 100*$^a$ | ca. 100*$^b$ | — |
| 1992-2013 Schultz P. & Hecht S. | Cell extract | ca. 25*$^c$ | ca. 6.4 | 12 |
| 2001-2013 Ueda T. | Purified comp. (all 20 aaRS) | 2*$^d$ | ca. 53 | 20 |

| Xaa-tRNA$^{Body\ seq.}$ | $K_D$ [nM] | Val-tRNA$^{Body\ seq.}$ | $K_D$ [nM] | $\Delta G°$ [kcal/mol] | Xaa-tRNA$_{NNN(Xaa)}$ | $K_D$ [nM] | $\Delta G°$ [kcal/mol] |
|---|---|---|---|---|---|---|---|
| Glu-tRNA$^{Glu2}$ | 43.6 | Val-tRNA$^{Glu2}$* | 0.5 | −11.7 | | | |
| Asp-tRNA$^{Asp1}$ | 28.3 | Val-tRNA$^{Asp1}$* | 1.9 | −11.0 | Asp-tRNA$^{YFA2}$ | >150.0 | <−8.6 |
| Gly-tRNA$^{Gly3}$ | 11.4 | Val-tRNA$^{Gly3}$ | 2.8 | −10.7 | Gly-tRNA$^{YFA2}$ | 62.0 | −9.1 |
| Thr-tRNA$^{Thr}$ | 16.1 | Val-tRNA$^{Thr3}$ | 4.0 | −10.5 | Thr-tRNA$^{YFA2}$ | 15.0 | −9.9 |
| Ala-tRNA$^{Ala1B}$ | 28.6 | Val-tRNA$^{Ala2}$ | 4.3 | −10.5 | Ala-tRNA$^{YFA2}$ | 100.0 | −8.8 |
| Cys-tRNA$^{Cys}$ | 13.6 | Val-tRNA$^{Cys}$ | 21.0 | −9.6 | | | |
| Leu-tRNA$^{Leu4}$ | 24.7 | Val-tRNA$^{Leu1}$ | 23.0 | −9.5 | | | |
| Met-tRNA$^{Met}$ | 10.6 | Val-tRNA$^{Met}$ | 33.0 | −9.4 | Met-tRNA$^{YFA2}$ | 17.0 | −9.8 |
| Pro-tRNA$^{Pro}$ | 12.6 | Val-tRNA$^{Pro3}$ | 34.0 | −9.3 | Pro-tRNA$^{YFA2}$ | 15.0 | −9.8 |
| Phe-tRNA$^{Phe}$ | 13.8 | Val-tRNA$^{Phe}$ | 48.0 | −9.2 | Phe-tRNA$^{YFA2}$ | 11.0 | −10.1 |
| Lys-tRNA$^{Lys1}$ | 43.5 | Val-tRNA$^{Lys}$ | 53.0 | −9.1 | Lys-tRNA$^{YFA2}$ | 35.0 | −9.4 |
| Arg-tRNA$^{Arg2}$ | 26.5 | Val-tRNA$^{Arg2}$ | 54.0 | −9.1 | Arg-tRNA$^{YFA2}$ | 17.0 | −9.8 |
| Ser-tRNA$^{Ser}$ | 15.9 | Val-tRNA$^{Ser1}$* | 61.3 | −9.1 | | | |
| Asn-tRNA$^{Asn}$ | 10.6 | Val-tRNA$^{Asn}$* | 88.3 | −8.9 | | | |
| Val-tRNA$^{Val1}$ | 92.0 | Val-tRNA$^{Val1}$ | 92.0 | −8.8 | Val-tRNA$^{YFA2}$ | 17.0 | −9.8 |
| Ile-tRNA$^{Ile}$ | 27.0 | Val-tRNA$^{Ile1}$ | 110.0 | −8.7 | Ile-tRNA$^{YFA2}$ | 8.1 | −10.3 |
| Trp-tRNA$^{Trp}$ | 9.9 | Val-tRNA$^{Trp}$* | 183.6 | −8.5 | Trp-tRNA$^{YFA2}$ | 3.6 | −10.7 |
| Gln-tRNA$^{Gln}$ | 5.7 | Val-tRNA$^{Gln2}$ | 250.0 | −8.3 | Gln-tRNA$^{YFA2}$ | 1.9 | −11.1 |
| Tyr-tRNA$^{Tyr2}$ | 15.7 | Val-tRNA$^{Tyr2}$ | 310.0 | −8.1 | | | |
| | | | | | $^L$Tyr-tRNA$^{Tyr}$ | 50.0 | −9.2 |
| | | | | | $^D$Tyr-tRNA$^{Tyr}$ | 1200.0 | −7.5 |

Dissociation constant of aa-tRNA and EF-Tu·GTP complex (column 4, 5, 7, 8) were re-presented from (Asahara, H., & Uhlenbeck, O. C. (2002). The tRNA Specificity of *Thermus thermophilus* EF-Tu. Proceedings of the National Academy of Sciences, 99(6), 3499-3504; Dale, T., Sanderson, L. E. & Uhlenbeck, O. C. The Affinity of Elongation Factor Tu for an Aminoacyl-tRNA Is Modulated by the Esterified Amino Acid†. *Biochemistry* 43, 6159-6166 (2004).); L- or D-Tyr-tRNA$^{Tyr}$ data are from (Yamane, T., Miller, D. L. & Hopfield, J. J. Discrimination between D- and L-tyrosyl transfer ribonucleic acids in peptide chain elongation. *Biochemistry* 20, 7059-7064 (1981)). For Xaa-tRNA$^{Body\ seq.}$ (column 2), $K_D$ of Phe and Leu are obtained first from the relative $K_D$ ratio of Val/Phe and Val/Leu4 from ((Louie, A., Ribeiro, N. S., Reid, B. R., & Jurnak, F. (1984). Relative affinities of all *Escherichia coli* aminoacyl-tRNAs for elongation factor Tu-GTP. Journal of Biological Chemistry, 259(8), 5010-5016, and then reference is made to $K_D$ of Phe and Leu for the remaining L-amino acids. When the same amino acids are acylated to different tRNA body sequences, the range of $K_D$ spans ca. 600-fold, and when various amino acids are acylated to same tRNA, the range of $K_D$ spans at least 80-fold based on the 13 tested amino acids. The L-Tyr acylated tRNA$^{Tyr}$ binds to EF-Tu·GTP 25-fold stronger than D-aminoacylated version. The dissociation constants are measured at 0° C., however, the same constant at 37° C. is 6-10 fold higher, calculated using $\Delta G°=-RT\ \ln(1/K_D)$. * Data converted from the measured $K_D$ of Phe-tRNA$^{Body\ seq}$.

The amount of all tRNA used in typical PURE translation (13-53 μM) is greater than that of EF-Tu (2-10 μM, See Table 2 below)

-continued

| Year, Lab | Translation system | [EF-Tu], μM | [aa-tRNA$^{aaRS}$], μM | [aa$^{mis}$-tRNA], μM |
|---|---|---|---|---|
| 2007-2013 Suga H. | Purified comp. (with 4 aaRS) | 10*$^e$ | ca. 13*$^f$ | 25-600 |
| 2014 This study | Purified comp. (with 6 aaRS) | 2, 25*$^g$ | ca. 18*$^f$ | 12-24 |

Figure 1D:
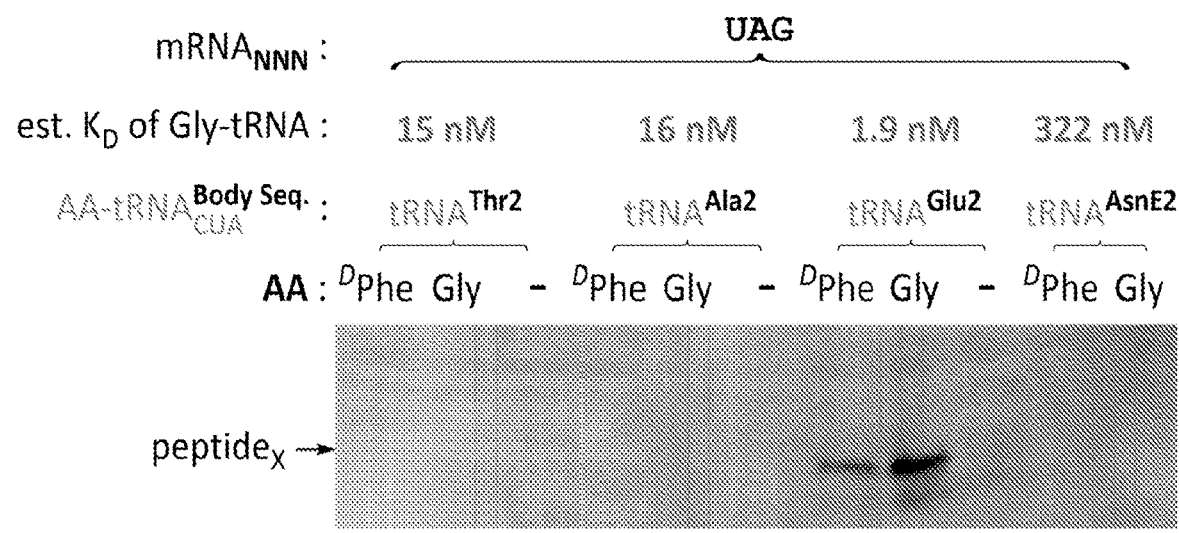
FIG. 1D depicts a Western blot of tests of various tRNA backbones with CUA anticodon for incorporation of Gly and $^{D}$Phe.
Figure 4:
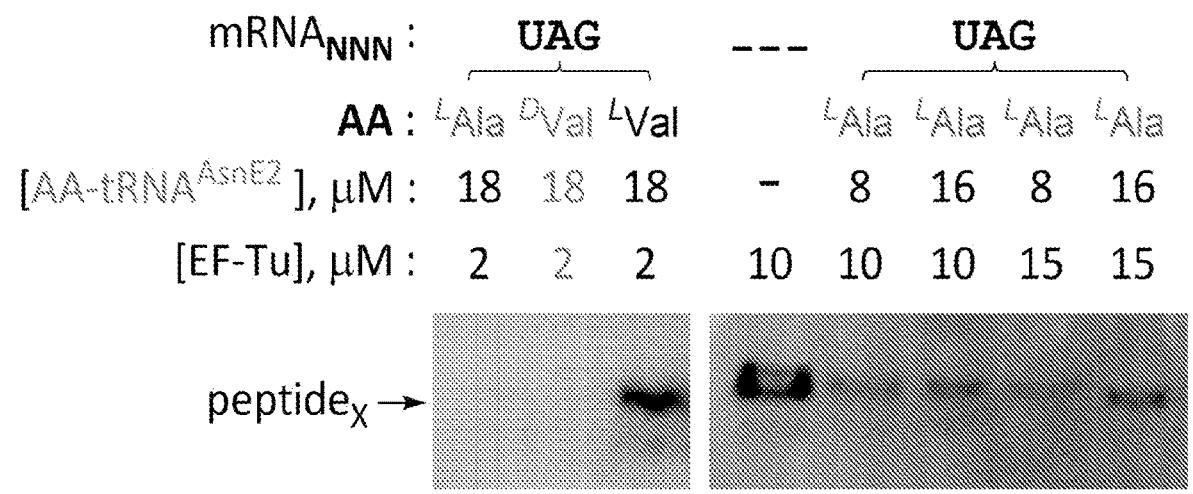
FIG. 4 is a gel image of an assay showing increasing either [$^L$Ala-tRNA$^{AsnE2}$] or [EF-Tu] or both improves incorporation rate.

The sequestering of EF-Tu could limit the EF-Tu access of chemically acylated $^{L/D}$AA-tRNAs. In addition, the fast kinetics of aminoacyl hydrolysis when not shielded by EF-Tu (see Hentzen, D., Mandel, P. & Garel, J.-P. Relation between aminoacyl-tRNA stability and the fixed amino acid. *Biochim. Biophys. Acta—Nucleic Acids Protein Synth.* 281, 228-232 (1972) and the lack of regeneration by aminoacyl-tRNA synthetases as in their competing normal $^L$AA-tRNA pairs lower amino acid incorporation yield. The present disclosure provides increasing the amount of EF-Tu to promote incorporation D-amino acids. Titrating the in vitro translation system with additional EF-Tu improves incorporating $^L$Ala carried by tRNA$^{AsnE2}$ (See FIG. 4). The disclosure provides the identification of tRNA bodies (Glu2, Thr2 and Ala2, naming convention following Fournier, M. J. & Ozeki, H. Structure and organization of the transfer ribonucleic acid genes of *Escherichia coli* K-12. *Microbiol. Rev.* 49, 379-397 (1985)) which exhibit strong affinities toward EF-Tu-GTP for use in incorporating weak EF-Tu binding $^{L/D}$AAs into peptides. See also Achenbach, J. et al. Outwitting EF-Tu and the ribosome: translation with d-amino acids. *Nucleic Acids Res.* 43, 5687-5698 (2015) in which tRNA$^{Gly}$ yield better delivery tRNA then tRNA$^{Tyr}$ when acylated with same $^D$AA. The present disclosure provides that Glu2 tRNA body outperforms Thr2, Ala2 and AsnE2 tRNA body in glycine incorporation, and also gives measurable $^D$Phe incorporation (See FIG. 1D).

Example IV

Figure 2A:
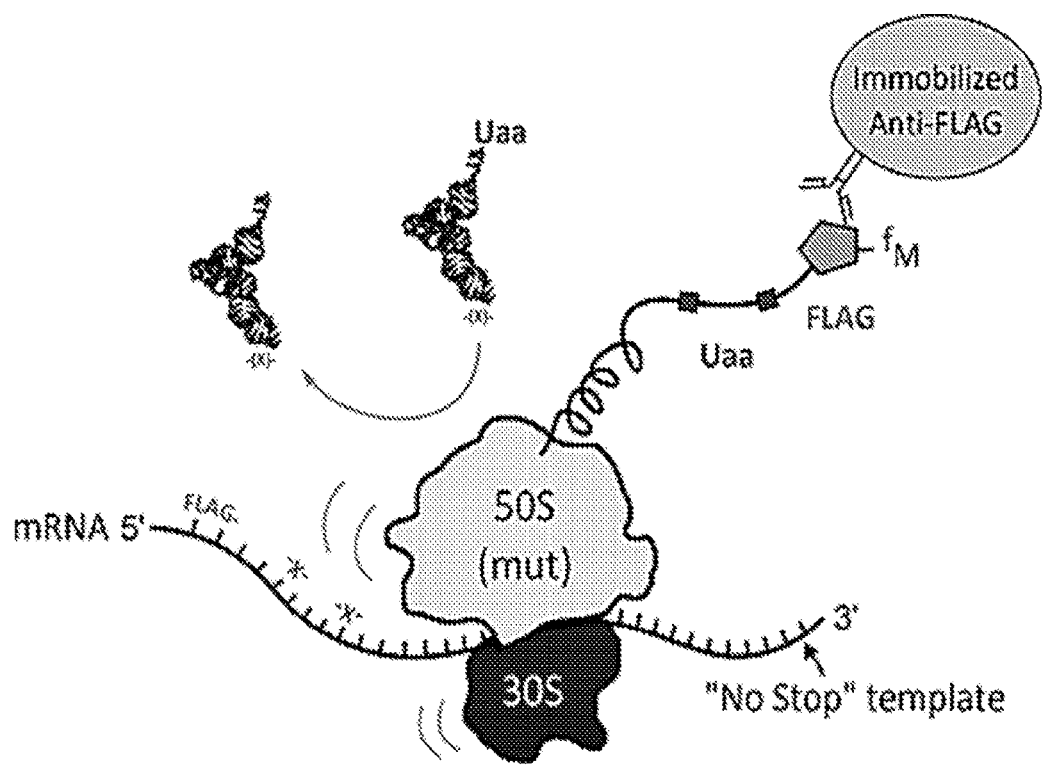
FIG. 2A depicts in schematic an in vitro selection platform for ribosome rRNA variants.
Figure 2B:
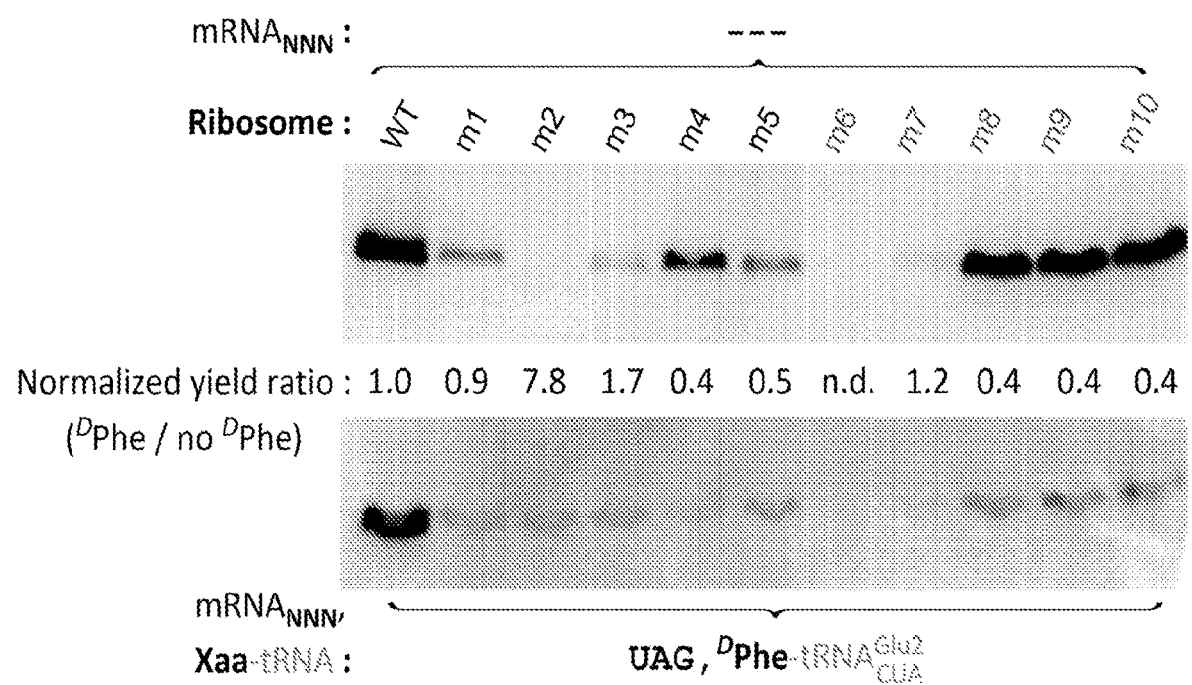
FIG. 2B depicts gel images of an assay of the ability of various ribosome rRNA variants to incorporate $^{D}$Phe.

Identifying Mutant Ribosomes with Enhanced D-Amino Acid Incorporation Capability The present disclosure provides the identification of ribosome mutants with enhanced $^D$AA incorporation capability. A $^D$AA read-through experiment is carried out along with the in vitro ribosome selection system developed by Cochella, L. & Green, R. Isolation of antibiotic resistance mutations in the rRNA by using an in vitro selection system. *Proc. Natl. Acad. Sci. U.S.A* 101, 3786-3791 (2004) hereby incorporated by reference in its entirety to an rRNA variants pool containing computer-randomized mutations around peptidyl transfer center (PTC). See FIG. 2A which depicts an in vitro selection platform for ribosome rRNA variants. The N-terminus FLAG-tag serves to identify active mutants when a ribosome reads through a few codons reassigned to $^D$AA or α, α-dialkylamino acid. 10 randomly picked variants after selection cycles are assayed for $^D$Phe incorporation activity. Mutants m2, m3 and m7 in FIG. 2B exhibit higher yield ratios of $^D$Phe-containing peptide versus no $^D$Phe-containing peptide synthesis than wild type ribosome.

Example V

Use of Elongation Factor P to Promote Incorporation of D-Amino Acids

The present disclosure provides the use of elongation factor P (EF-P) to promote incorporation of D-amino acids into a growing polypeptide chain using translational machinery. Elongation factor P is a prokaryotic protein translation factor used in peptide bond synthesis on 70S robosomes from fMet-tRNAfMet. See Aoki et al., *Biochimie* 79(1):7-11 (1997) hereby incorporated by reference in its entirety. Elongation factor P includes three domains: an N-terminal KOW-like domain, a central OB domain which forms an oligonucleotide-binding fold, and a C-terminal domain which adopts an OB-fold, with five beta-strands forming a beta-barrel in a Greek-key topology. See Hanawa-Suetsugu et al., Proc. Natl. Acad. Sci. U.S.A. 101(26) 9595-9600 (2004) hereby incorporated by reference in its entirety.

Figure 2C:
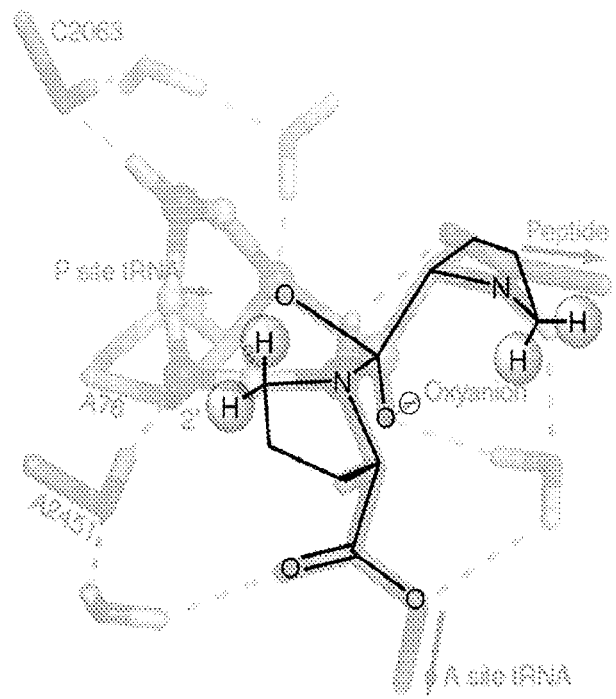
FIG. 2C depicts use of a substrate assistance mechanism to show two D-amino acids occupying the peptidyl transfer center (PTC).
Figure 2D:
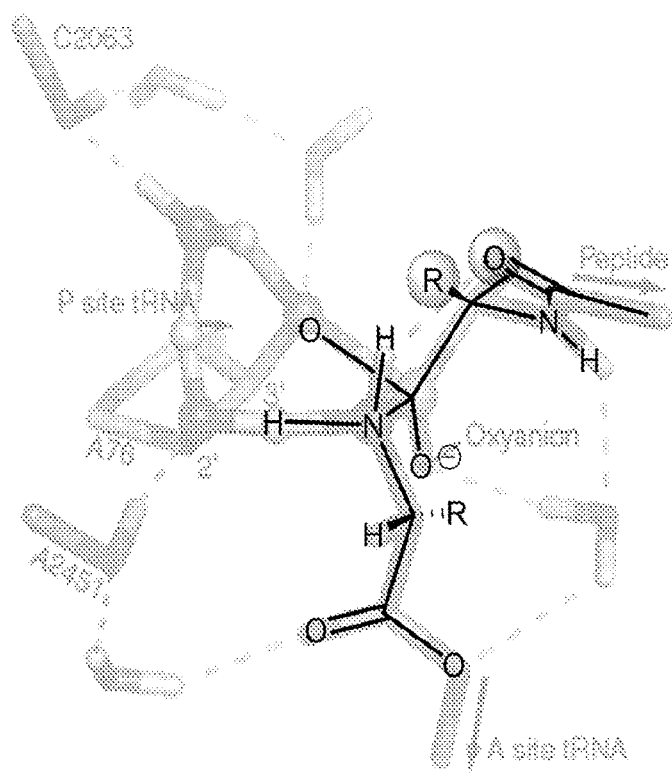
FIG. 2D depicts two L-prolines present in the peptidyl transfer center.

Misalignment of $^D$AA atoms in the peptidyl transfer center (PTC) due to steric clashes with rRNA may abolish the substrate-assisted catalysis mechanism. See FIG. 2C which depicts a substrate assisted mechanism modeled by Wallin, G., & Åqvist, J. (2010). The transition state for peptide bond formation reveals the ribosome as a water trap. *Proceedings of the National Academy of Sciences,* 107(5), 1888-1893 hereby incorporated by reference in its entirety overlaid with proposed situations where two $^D$AAs occupied PTC. FIG. 2D depicts two L-prolines present in the PTC to illustrate the disruption of the hydrogen bond network. Atoms or groups (R) marked with spheres are where new anticipated steric clashes may be formed.

Figure 3:
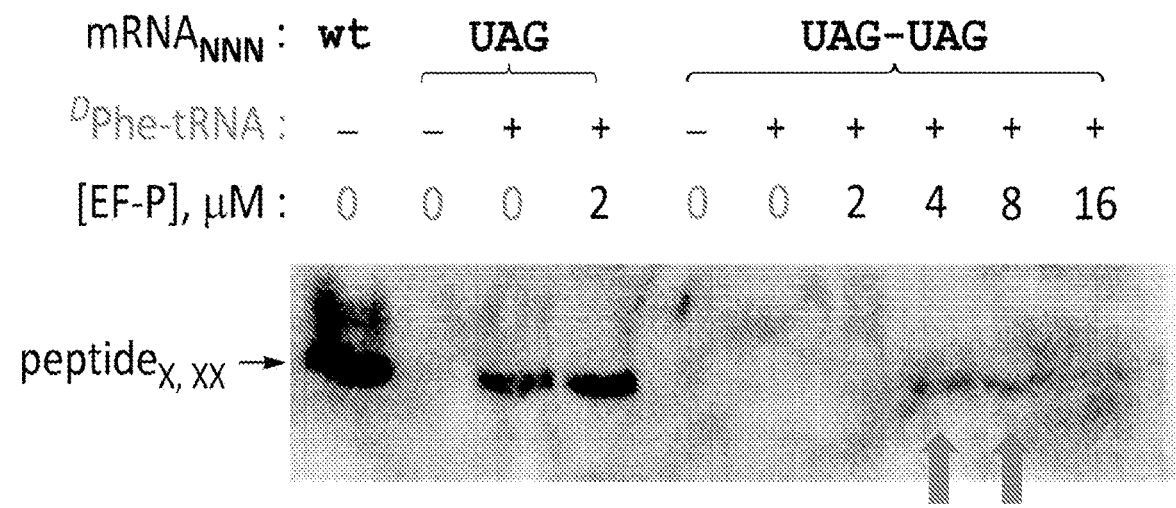
FIG. 3 depicts a gel image of an assay showing the effect of EF-P on $^{D}$Phe incorporation.

The present disclosure provides de novo PTC catalysis for $^D$AA in rRNA using elongation factor P (EF-P) which has been reported to resolve ribosome stalling upon incorporating consecutive polyprolines. See Doerfel, L. K. et al. EF-P is essential for rapid synthesis of proteins containing consecutive proline residues. *Science* 339, 85-8 (2013) and Ude, S. et al. Translation elongation factor EF-P alleviates ribosome stalling at polyproline stretches. *Science* 339, 82-5 (2013). Consecutive L-proline stalling may result from its secondary amine structure that causes steric clash and abolishes the ribosome catalysis mechanism. See FIG. 2D. EF-P was tested in the $^D$AA read-through experiment described herein. With 2 μM of EF-P, single $^D$Phe read-through is promoted. EF-P at 4-8 μM provides a significant consecutive $^D$Phe-$^D$Phe read-through event. See FIG. 3.

The invention claimed is:

1. A method of making a polypeptide including one or more D-amino acids comprising
combining protein translation factors including (1) a ribosome, (2) a template encoding the polypeptide, wherein the template encoding the polypeptide includes one or more codons which have been recoded to accept a tRNA attached to a D-amino acid, (3) a plurality of L-amino acids and a plurality of corresponding tRNAs, (4) a plurality of D-amino acids and their corresponding aminoacyl tRNA synthetase or a plurality of tRNAs ligated with a D-amino acid, and (5) elongation factor P in a concentration of 4 to 8 micromolar,
wherein translation of the template encoding the polypeptide occurs to produce the polypeptide including one or more D-amino acids.

2. The method of claim 1 wherein the one or more codons are amber stop codons.

3. The method of claim 1 wherein the template is a mRNA template encoding the polypeptide.

4. The method of claim 1 wherein the template is a DNA template encoding the polypeptide.

5. The method of claim 1 wherein the tRNA corresponding to the D-amino acids have a high binding affinity to elongation factor thermo unstable.

6. The method of claim 1 wherein the tRNA corresponding to the D-amino acids are backbone-optimized to promote binding between the tRNA and elongation factor thermo unstable.

7. The method of claim 1 wherein the ribosome is a mutant ribosome having enhanced $^D$AA incorporation capability compared to a wild type ribosome.

8. The method of claim 1 carried out in an in vitro protein synthesis solution.

9. The method of claim 1 wherein the ribosome is an 80S ribosome.

10. A method of making a polypeptide including one or more D-amino acids comprising
combining protein translation factors including (1) a ribosome, (2) a template encoding the polypeptide, wherein the template encoding the polypeptide includes one or more codons which have been recoded to accept a tRNA attached to a D-amino acid, (3) a plurality of L-amino acids and a plurality of corresponding tRNAs, (4) a plurality of D-amino acids and their corresponding aminoacyl tRNA synthetase or a plurality of tRNAs ligated with a D-amino acid, and (5) elongation factor P in a concentration of 4 to 16 micromolar,
wherein translation of the template encoding the polypeptide occurs to produce the polypeptide including one or more D-amino acids.

11. The method of claim 10 wherein the one or more codons are amber stop codons.

12. The method of claim 10 wherein the template is a mRNA template encoding the polypeptide.

13. The method of claim 10 wherein the template is a DNA template encoding the polypeptide.

14. The method of claim 10 wherein the tRNA corresponding to the D-amino acids have a high binding affinity to elongation factor thermo unstable.

15. The method of claim 10 wherein the tRNA corresponding to the D-amino acids are backbone-optimized to promote binding between the tRNA and elongation factor thermo unstable.

16. The method of claim 10 wherein the ribosome is a mutant ribosome having enhanced $^D$AA incorporation capability compared to a wild type ribosome.

17. The method of claim 10 carried out in an in vitro protein synthesis solution.

18. The method of claim 10 wherein the ribosome is an 80S ribosome.

* * * * *